(12) United States Patent
Yamashita et al.

(10) Patent No.: US 10,160,949 B2
(45) Date of Patent: Dec. 25, 2018

(54) AGENT FOR IMPROVING SPERM-MOTILITY

(71) Applicants: Naoki Yamashita, Kanagawa (JP); Tokyo Metropolitan Geriatric Hospital and Institute of Gerontology, Tokyo (JP)

(72) Inventors: Naoki Yamashita, Kanagawa (JP); Kumiko Nakata, Kanagawa (JP); Ikuroh Ohsawa, Tokyo (JP)

(73) Assignees: Tokyo Metropolitan Geriatric Hospital and Institute of Gerontology, Tokyo (JP); Naoki Yamashita, Kanagawa (JP)

( * ) Notice: Subject to any disclaimer, the term of this patent is extended or adjusted under 35 U.S.C. 154(b) by 0 days.

(21) Appl. No.: 15/032,446

(22) PCT Filed: Oct. 30, 2014

(86) PCT No.: PCT/JP2014/005506
§ 371 (c)(1),
(2) Date: Apr. 27, 2016

(87) PCT Pub. No.: WO2015/064109
PCT Pub. Date: May 7, 2015

(65) Prior Publication Data
US 2016/0281057 A1 Sep. 29, 2016

(30) Foreign Application Priority Data

Oct. 31, 2013 (JP) .................................. 2013-227297

(51) Int. Cl.
*C12N 5/076* (2010.01)
*A61K 33/00* (2006.01)

(52) U.S. Cl.
CPC .............. *C12N 5/061* (2013.01); *A61K 33/00* (2013.01); *C12N 2500/02* (2013.01)

(58) Field of Classification Search
None
See application file for complete search history.

(56) References Cited

U.S. PATENT DOCUMENTS

| 3,655,172 A * | 4/1972 | Ingels | B01F 3/04439 |
| | | | 252/373 |
| 2008/0299535 A1 | 12/2008 | Tokuda et al. | |
| 2009/0035383 A1 | 2/2009 | Ohta et al. | |
| 2009/0246290 A1 | 10/2009 | Ohta et al. | |
| 2011/0111048 A1 | 5/2011 | Satoh et al. | |

FOREIGN PATENT DOCUMENTS

| JP | 2000-517311 | 12/2000 |
| JP | 2005-087257 | 4/2005 |
| JP | 2005-213147 | 8/2005 |
| JP | 2010-240376 | 10/2010 |
| JP | 2010-259722 | 11/2010 |
| WO | 2005/115141 | 12/2005 |
| WO | 2007/021034 | 2/2007 |
| WO | 2008/026785 | 3/2008 |
| ZA | 9707669 | 2/1998 |

OTHER PUBLICATIONS

Kawasaki et al., Biochemical and Biophysical Research Communications, 2010, vol. 397, p. 608-613.*
Talwar, P., "Update on Sperm banking", Chapter 22, of E. Seli and A. Agarwal (eds.), Fertility Preservation: Emerging Technologies and Clinical Applications, Springer Science+Business Media, LLC 2012, p. 289-301.*
O'Connell et al., Human Reproduction, 2002, vol. 17, No. 3, p. 704-709.*
Ohsawa et al., Nature, 2007, vol. 13, No. 6, p. 688-694.*
English Translation of International Preliminary Report on Patentability for PCT/JP2014/005506 dated May 12, 2016.
Chuai et al., "Hydrogen-rich saline protects spermatogenesis and hematopoiesis in irradiated BALB/c mice," Med. Sci Monit., 2012, vol. 18(3): pp. BR89-BR94.
Condorelli et.al., "Myoinositol: does it improve sperm mitochondrial function and sperm motility?," Urology, 79: 1290-1295 (2012).
Gupta et al., "The Role of Oxidative Stress and Antioxidants in Assisted Reproduction," Current Women's Health Reviews, 2010, vol. 6, No. 3, pp. 227-238.
Mitsuzuka et al., "Effects of Hydrogen Molecule on Oxidative Stress of Bovine Spermatozoa Undergoing Freezing and Thawing," 2011, vol. 57, Suppl., P. J119, No. OR2-9 (Partial Translation Included).
Ohsawa, "Molecular Hydrogen Medicine: Current Status and Future Challenges," Japan Society for Biomedical Gerontology, 35(1);1-7, 2011 (Partial Translation Included).
Oono et al., "Effects of Reactive Oxygen Species and Antioxidants on the Motility of Boar Spermatozoa in the Process of Freezing and Thawing," 2001, Jpn. J. Swine Science, vol. 38, No. 1, 12-19 (Partial Translation Included).

* cited by examiner

*Primary Examiner* — Kade Ariani
(74) *Attorney, Agent, or Firm* — Occhiuti & Rohlicek LLP

(57) ABSTRACT

The present invention addresses the problem of providing an agent for improving sperm-motility, in particular, an agent for improving forward-sperm-motility, for use on reduced-motility sperm in male infertility treatment. Prepared is a gaseous agent for improving sperm-motility consisting of a gas that contains hydrogen molecules in the amount of 1% (v/v) or higher, for example, a gas that contains hydrogen molecules in an amount of between 45 and 55% (v/v), or a liquid agent for improving sperm-motility consisting of a liquid such as physiological saline, a culture solution, or a buffer solution containing hydrogen molecules in the amount of 1% or higher of the saturation solubility thereof, for example, a liquid in which hydrogen molecules have been dissolved by bubbling.

9 Claims, 6 Drawing Sheets

[Figure 1]
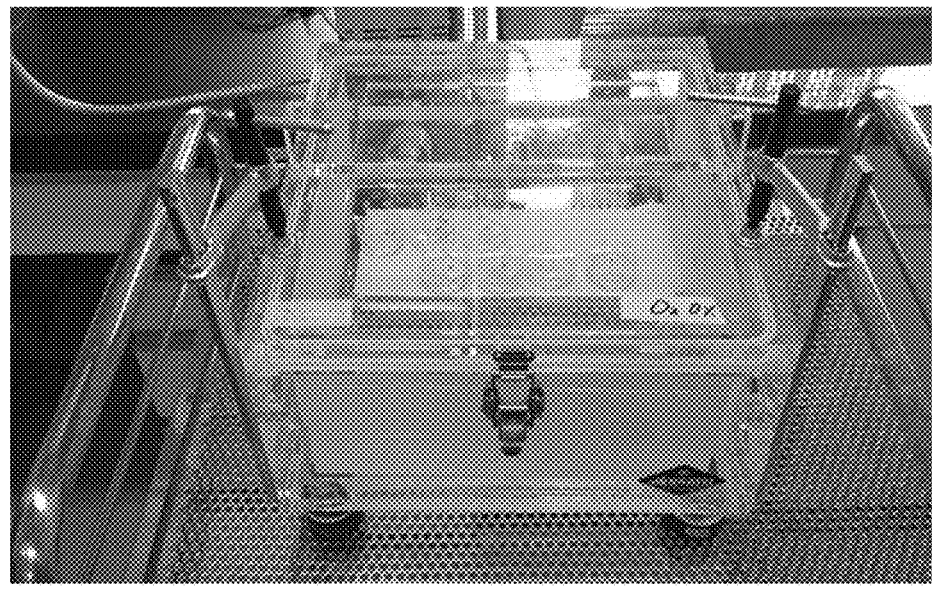
[Figure 2]
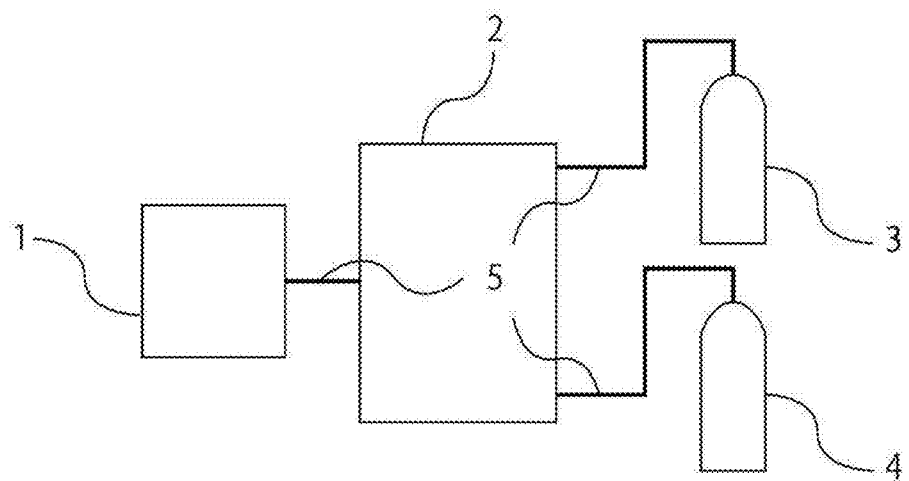

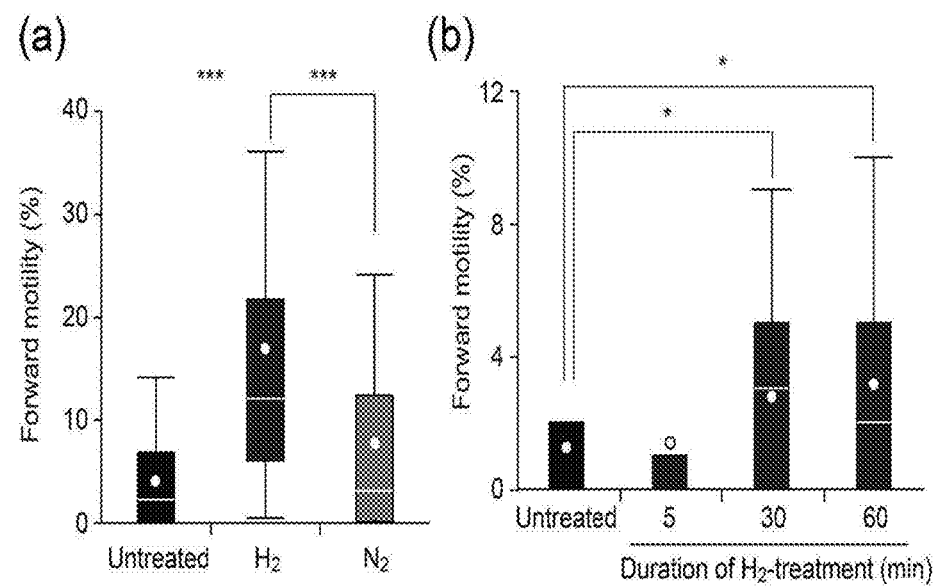
[Figure 3]

[Figure 4]
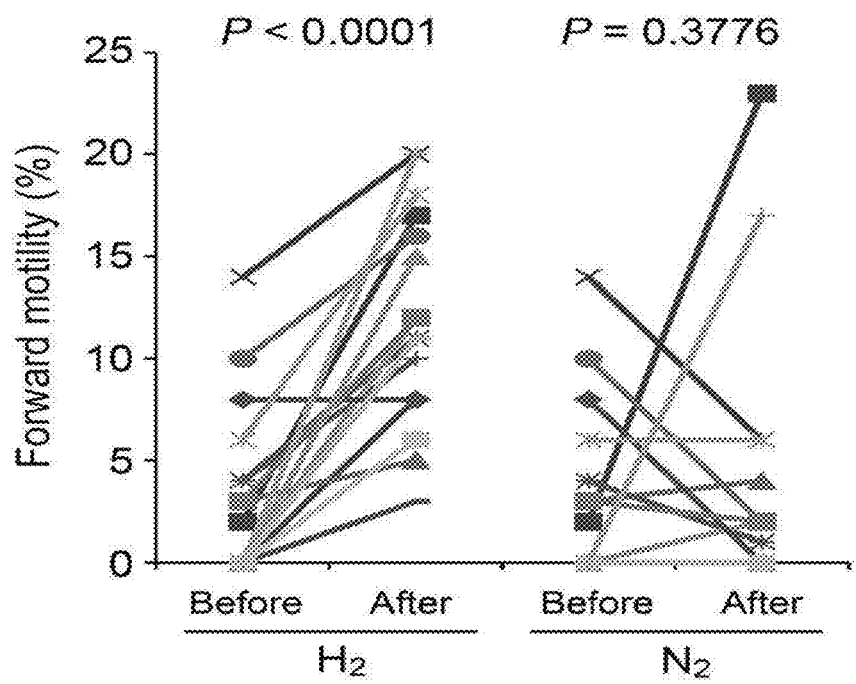
[Figure 5]
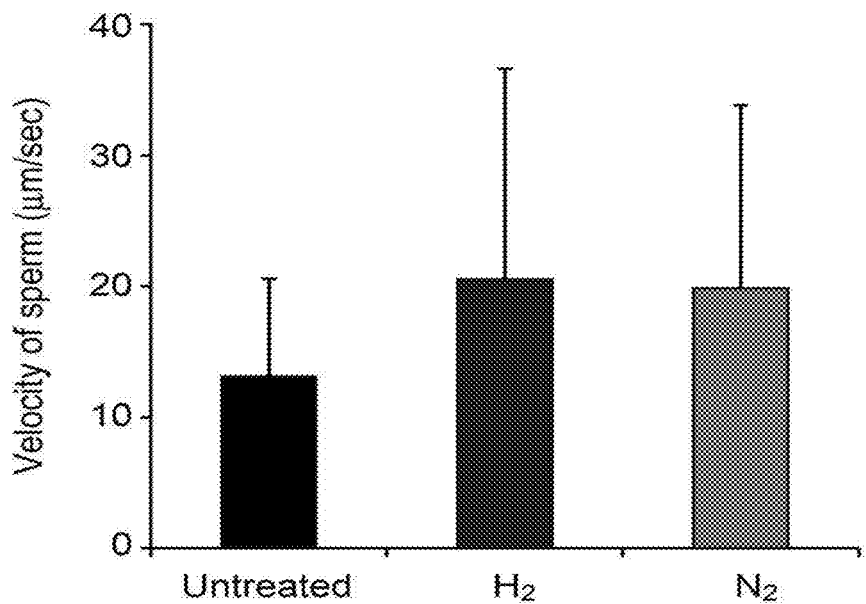

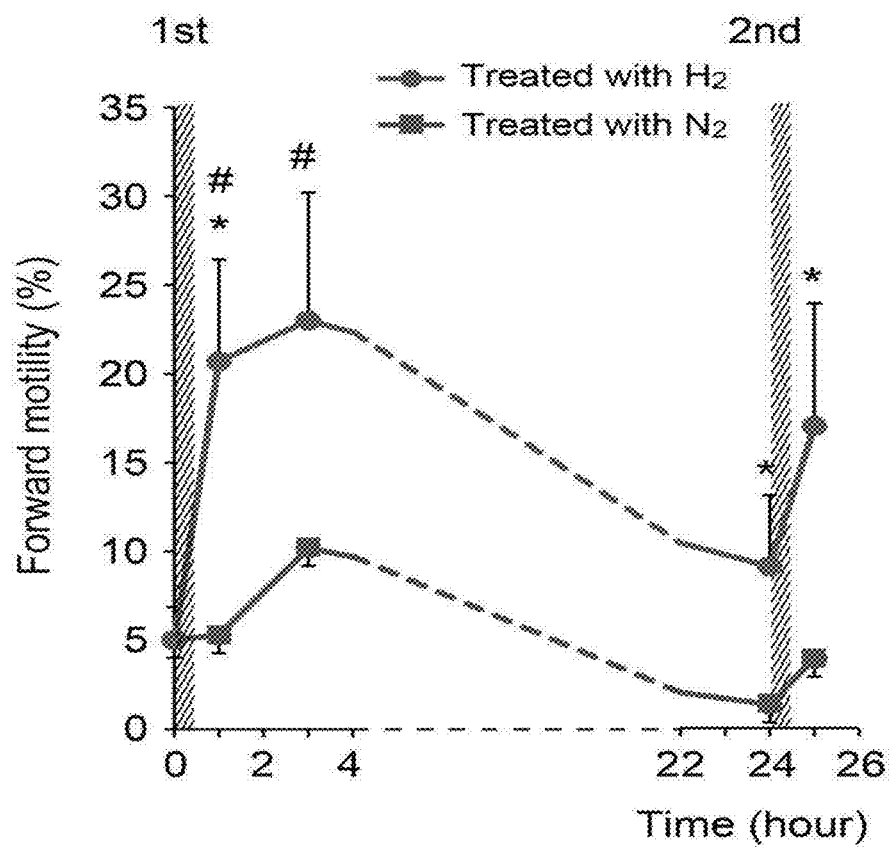
[Figure 6]

[Figure 7]
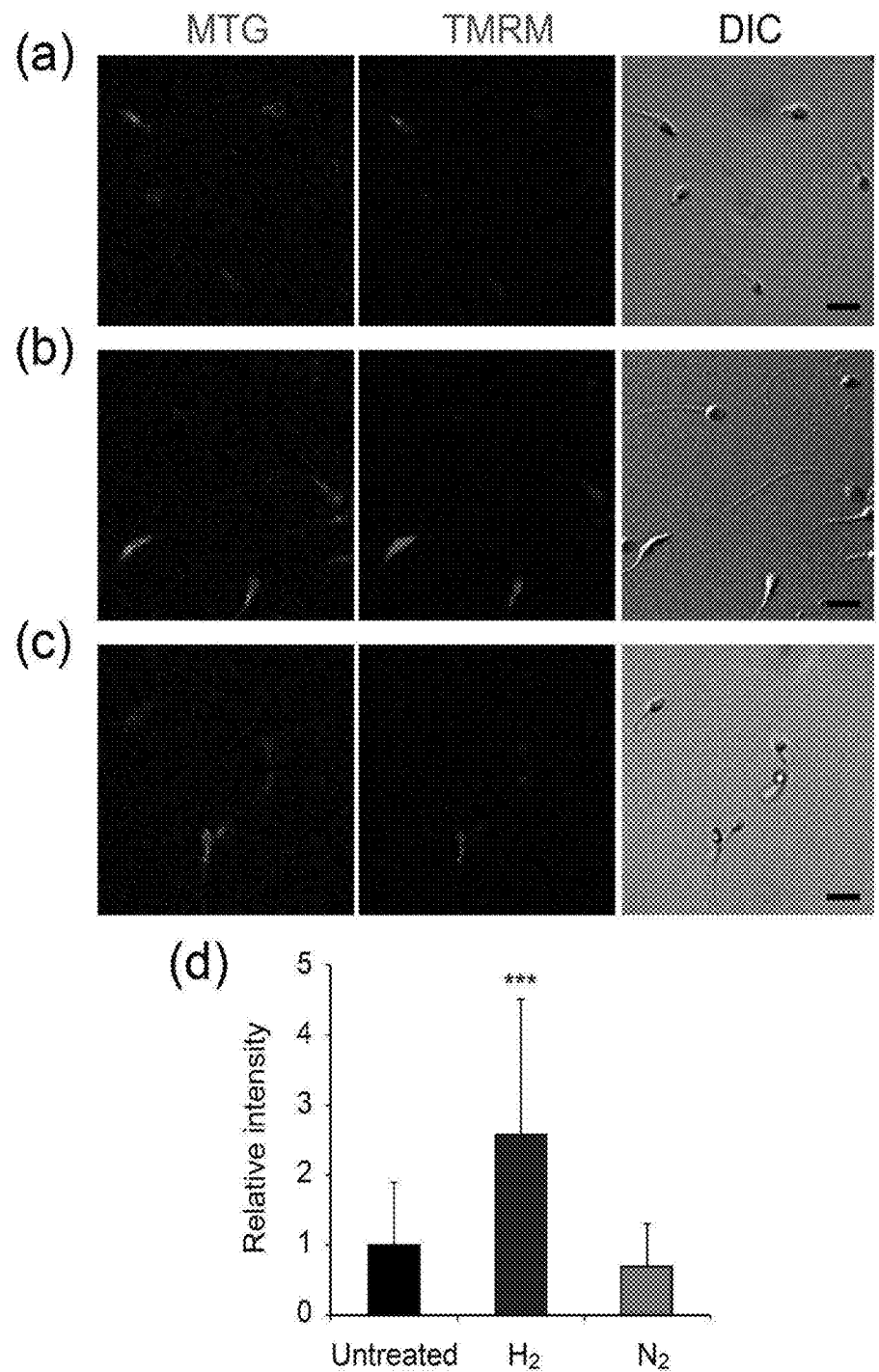

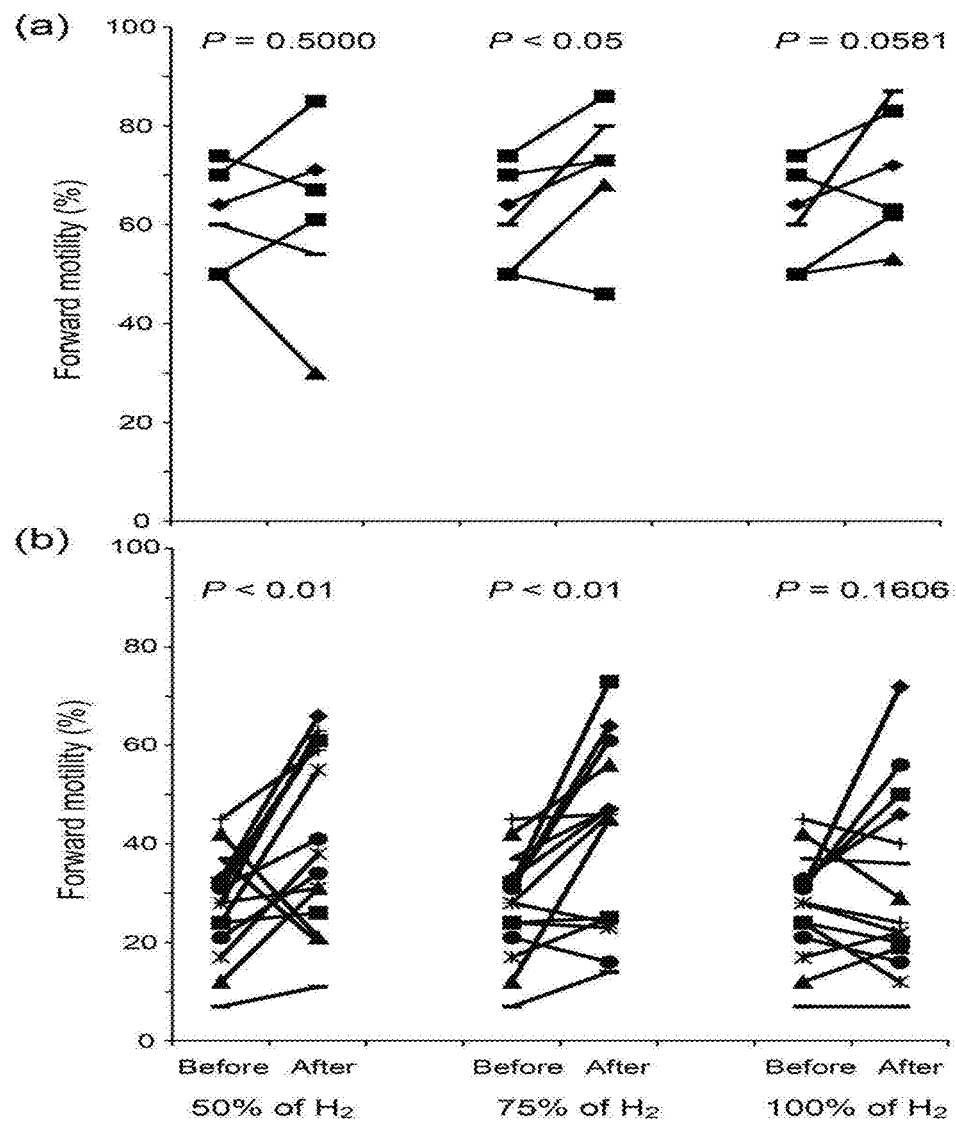
[Figure 8]

AGENT FOR IMPROVING SPERM-MOTILITY

CROSS REFERENCE TO RELATED APPLICATIONS

This application is a National Stage of International Application No. PCT/JP 2014/ 005506 filed on Oct. 30, 2014, which claims priority to Japanese Application No. 2013-227297 filed on Oct. 31, 2013, the contents of which are hereby incorporated by reference in their entirety.

TECHNICAL FIELD

The present invention relates to agents for improving sperm-motility that contain hydrogen molecules as an active ingredient and can increase the motility of sperm, in particular, the forward motility or the migration distance of forwardly moving sperm, thereby raising the fertilization rate.

BACKGROUND ART

According to the WHO (World Health Organization), the case where "only a man" has a problem accounts for 24% of the causes of infertility. When the case where both a man and a woman have problems is added, men are involved in about 50% of all the cases. However, the infertility treatment in Japan is placed on the women's side, so that there is currently almost no measure on the men's side.

The causes of male infertility are classified into hypospermia, the case where the volume of semen ejaculated is small, oligozoospermia, the case where the number of sperm is small, and azoospermia, the case where no sperm exist in semen. In addition, the case where the motility of sperm is low is diagnosed as asthenospermia. However, why does the number of sperm decrease and why is the motility rate reduced? These causes can be specified only in a few cases and about 60% of the causes of male infertility remain unclear.

The azoospermia is further divided into two and classified into obstructive azoospermia and non-obstructive azoospermia. Obstructive azoospermia is a pathology in which while sperm are normally formed in the testicles, no sperm come out into ejaculatory semen due to the abnormality of the epididymis and seminal duct. Meanwhile, non-obstructive azoospermia is a pathology in which because of the spermatogenic dysfunction of the testicles themselves, no sperm are formed. For this diagnosis, it is important to check whether or not the blood level of gonadotropin (e.g., FSH, LH), as determined by collecting blood, is abnormal, whether or not the volume and elasticity of the testicles are decreased, and whether or not the vas deferens is unobstructed. The level of serum gonadotropin is an index of spermatogenic function at that time point. The azoospermia having the level of FSH within a normal range means the case where while sperm is generated, none of them come out into ejaculatory semen. Accordingly, the case is diagnosed as obstructive azoospermia. The case where the level of FSH is markedly low or high is diagnosed as non-obstructive azoospermia.

In the non-obstructive azoospermia case where there are sperm verified by testis biopsy, there are many immature or abnormal sperm, the most of which are immotile sperm. Use of such immotile sperm in micro-insemination results in a very low conception rate. Because of this, after the viability of sperm is checked using an HOS test (hypo-osmotic swelling test), micro-insemination is carried out in some facilities (Jeyendran R S, et al., J Reprod Fertil., 1984; 70: 219-28). However, although the HOS test, in which sperm are immersed in a culture solution with a low osmotic pressure, is used to check whether or not the sperm are viable, use of the sperm in micro-insemination is technically difficult. The case where sperm lack motility, not only inside the testicles, but also in ejaculatory semen, has been reported such that the rates of fertilization and embryogenesis by micro-insemination and the conception rate after implantation are extremely low (Vandervorst M, et al., Hum Reprod. 1997; 12: 2429-33). In clinical practice, motile normal-shaped sperm are selected and used for micro-insemination.

In addition, cryopreserved sperm are routinely used in reproductive treatment. However, the freezing treatment reportedly causes a change in the morphology of sperm, the change including damage on mitochondria of sperm; in particular, there is a report in which the freezing treatment largely affects the motility of sperm (O'Connell M, et al., Hum Reprod., 2002; 17: 704-9) (Boitrelle F, et al., J Androl., 2012; 33: 1371-8). There is no reported approach clinically effective in activating sperm having reduced motility subjected to freezing treatment.

Flagellar movement, which is driving force of the motility of sperm, is mediated through motor protein dyneins (Gibbons I R, et al., Science, 1965; 149: 424-426) and tubulins, which constitute a cytoskeletal microtubule serving as a rail (Mohri H, Nature, 1968; 217: 1053-54). The flagellar movement is based on the dynein-mediated sliding of microtubules (Summers K E, et al., Proc. Nat. Acad. Sci. USA, 1971; 68: 3092-3096). The sliding of microtubules causes the bending of a flagellum (Shingyouji, et al., Nature, 1977; 265: 269-270). These phenomena were already uncovered in 1970's. However, the mechanism of flagellar bending at the base and the mechanism of bending wave transmission remain unclear. The flagellar movement is powered by ATP. The ATP that has been synthesized in mitochondria seems to be consumed at each part of a flagellum while the ATP diffuses (Steeghs, et al., Biochem. Biophys. Acta., 1995; 30: 130-138). Meanwhile, there is also a report in which the sperm under an anaerobic condition, for example, in the uterus or oviduct of a mouse or cow, depend on the ATP that has been synthesized in the glycolytic pathway that does not need oxygen (Mukai, et al., Biol. Reprod., 2004; 71: 540-547).

The ATP production in mitochondria needs oxygen. Sperm, one of cells that need oxygen, are known to be affected by reactive oxygen species such as hydrogen peroxide, a superoxide anion, and a hydroxyl radical (Aitken, et al., J. Reprod. Fertil., 1987; 81: 459-469). The superoxide anion, etc., plays a role in making sperm super active and in acquiring fertility, but has different functions depending on, for example, the site or period of action. Meanwhile, seminal plasma contains catalase, superoxide dismutase (SOD), and the like, which can remove reactive oxygen species, so that excessive reactive oxygen species can be removed. Due to this, the sperm, from which seminal plasma has been washed away for use in infertility treatment, are likely to be exposed to reactive oxygen species.

Oxidative stress occurs because reactive oxygen species or free radicals, which have strong oxidation power, are generated in excess. Among them, potent hydroxyl radicals are known to impart various harmful effects on the living body. An approach to eliminating hydroxyl radicals by using an antioxidant and effects thereof have been examined. For example, hydrogen molecules characteristics of selectively reducing and inactivating toxic radicals such as a hydroxyl radical were utilized. This examination involved experimental animal models in which the inhibition of brain ischemia or reperfusion injury and the inhibition of atherosclerosis were exhibited (Non-Patent Document 1). In addition, there are reports on, for example, an improvement in lipid metabolism (Patent Document 1), possible use of a hydrogen-containing agent in the treatment of lung inflammation (Patent Document 2), and a method of inhaling a hydrogen gas for the purpose of aiming at health promotion effects (Patent Document 3). Also, there is a report demonstrating that regarding the motility of sperm, addition of myoinositol to a sperm suspension promotes the recovery of mitochondrial functions, thereby enhancing the motility of sperm (Non-Patent Document 2). This examination, however, is involved in the motile sperm that are ejaculated on the day of collection and can be used for the treatment of in vitro fertilization or micro-insemination. Thus, the above cannot provide a solution to the problem of clinically using immotile sperm. Further, no report has addressed the connection between hydrogen molecules and the motility of sperm.

PRIOR ART DOCUMENTS

Patent Documents

Patent Document 1: Re-publication of PCT International Publication No. 2008-026785
Patent Document 2: Japanese unexamined Patent Application Publication (Translation of PCT Application) No. 2000-517311
Patent Document 3: Japanese unexamined Patent Application Publication No. 2005-087257

Non-Patent Documents

Non-patent Document 1: Ikuroh Ohsawa, "Molecular Hydrogen Medicine: Current Status and Future Challenges", Biomedical Gerontology, 35(1); 1-7, 2011.
Non-patent Document 2: Condorelli, et. al., Urology, 2012 June; 79(6): 1290-5.

SUMMARY OF THE INVENTION

Object to be Solved by the Invention

The present invention addresses the problem of providing an agent for improving sperm-motility, in particular, an agent for improving forward-sperm-motility, for use on reduced-motility sperm in male infertility treatment.

Means to Solve the Object

The present inventors have conducted intensive research so as to solve the above problem. In the course of the research, test samples were sperm that were collected for infertility treatment and were then to be disposed as waste, and that had a passage of five or more days after ejaculation and had markedly decreased motor functions. Subsequently, a gas containing highly concentrated hydrogen molecules was contacted with a sperm suspension. Then, the present inventors found out the recovery of the forward motility of the sperm and a remarkable increase in the forward migration distance. The present inventors also found out the recovery of the forward motility when the sperm with reduced motor functions were contacted with a culture solution in which hydrogen molecules had been dissolved. Further, the present inventors found out the recovery of the forward motility when the cryopreserved sperm were washed with a culture solution in which hydrogen molecules had been dissolved. The present invention has been completed on the basis of these findings.

Specifically, the present invention will be described as follows:

(1) an agent for improving sperm-motility, consisting of a gas comprising a hydrogen molecule in an amount of 1% (v/v) or higher,
(2) the agent for improving sperm-motility according to the above (1), wherein the gas comprising a hydrogen molecule in an amount of 1% (v/v) or higher is a gas comprising a hydrogen molecule in an amount of between 45 and 55% (v/v),
(3) the agent for improving sperm-motility according to the above (1) or (2), wherein the gas is a mixed gas of a hydrogen gas, an oxygen gas, a carbon dioxide gas, and a nitrogen gas,
(4) an agent for improving sperm-motility, consisting of a liquid comprising a hydrogen molecule in an amount of 1% or higher of a saturation solubility thereof,
(5) the agent for improving sperm-motility according to the above (4), wherein the hydrogen molecule is dissolved by bubbling,
(6) the agent for improving sperm-motility according to the above (4) or (5), wherein the liquid is physiological saline, a culture solution, or a buffer solution, comprising the hydrogen molecule,
(7) the agent for improving sperm-motility according to any one of the above (4) to (6), which is stored in a container,
(8) the agent for improving sperm-motility according to any one of the above (1) to (7), which improves sperm forward motility,
(9) the agent for improving sperm-motility according to any one of the above (1) to (8), wherein the sperm is a cryopreserved sperm,
(10) a method of improving motility of a sperm, comprising contacting the agent for sperm-motility according to any one of the above (1) to (9) with the sperm in vitro,
(11) the method according to the above (10), further comprising contacting the agent for improving sperm-motility with the sperm a plurality of times,
(12) use of hydrogen molecules in the preparation of a gaseous or liquid agent for improving sperm-motility,
(13) a hydrogen molecule for improving sperm motility, and
(14) a treatment container for improving sperm motility, comprising: a port for introducing a gas comprising a hydrogen molecule; and a port for discharging the introduced gas.

Effect of the Invention

The present invention provides a novel treatment protocol such that the forward motility of immotile sperm, which do not have motility and to which there is currently no available solution, is recovered. In addition, it is possible to recover the forward mobility of cryopreserved sperm and have reduced motility, so that the burden caused by sperm collection can be reduced. The present invention will bring a promising technology, which should increase a conception rate, to cases of infertility treatment where the cause is on the man side and immotile sperm have to be used for micro-insemination while a couple accepts that the conception rate is markedly deteriorated when compared with the case of using sperm with forward motility. In particular, this technology is for patients being treated that include male infertility patients who have to use their sperm without motor functions, such as sperm in the testicles, or round spermatids, which are immature as sperm, for the treatment.

BRIEF DESCRIPTION OF DRAWINGS

FIG. 1 is a photograph of a container for treatment using an agent for improving sperm-motility according to the present invention.

FIG. 2 is a schematic diagram of an apparatus for treatment using an agent for improving sperm-motility according to the present invention.

FIG. 3(a) is a graph showing the percentage of sperm with forward motility after the sperm that had had a passage of five days or more after collection were subjected to $H_2$ treatment or $N_2$ treatment. FIG. 3(b) is a graph showing the correlation between the duration of treatment and the percentage of sperm with forward motility with respect to the sperm that had a passage of five days or more after collection and were then subjected to $H_2$ treatment.

FIG. 4 is a graph showing the results of individual samples with respect to the percentage of sperm with forward motility before and after the sperm that had a passage of five days or more after collection were subjected to $H_2$ treatment or $N_2$ treatment.

FIG. 5 is a graph showing a migration distance per second of sperm with forward motility after the sperm that had stayed five days or more after collection were subjected to $H_2$ treatment or $N_2$ treatment.

FIG. 6 is a graph showing a time course of the percentage of sperm with forward motility, when the sperm that had a passage of 5 days or more after collection were subjected to $H_2$ treatment or $N_2$ treatment, in the sperm re-treated at 24 hours after the first treatment.

FIG. 7 is images obtained while sperm subjected to (a) no treatment, (b) $H_2$ treatment, or (c) $N_2$ treatment were co-stained with a dye sensitive to mitochondrial membrane potential and then scanned under a laser scanning confocal microscope. FIG. 7(d) is a graph showing the results of semi-quantifying, using the ImageJ, the fluorescent intensity of the sperm stained with the dye sensitive to mitochondrial membrane potential.

FIG. 8 is graphs showing the results of individual samples with respect to the percentage of sperm with forward motility when the sperm that had been subjected to freeze-thawing were treated with different concentrations of $H_2$. In FIG. 8(a), the subjects are samples obtained from patients in which the percentage of sperm with forward motility was 50% or higher. In FIG. 8(b), the subjects are samples obtained from patients in which the percentage of sperm with forward motility was less than 50%.

MODE OF CARRYING OUT THE INVENTION

An agent for improving sperm-motility according to the present invention consists of a gas containing hydrogen molecules in an amount of 1% (v/v) or higher or a liquid containing hydrogen molecules in an amount of 1% or higher of the saturation solubility thereof. The agent for improving sperm-motility is not particularly limited as long as the sperm are contacted with hydrogen molecules for treatment. The agent for improving sperm-motility according to the present invention causes the motility of sperm derived from male infertility patients, in particular, the forward motility to be recovered, thereby increasing the possibility of the conception achieved by micro-insemination As used herein, improvements in the motility of sperm are described in the "Semen Examination Standardization Guidelines" edited by the Japanese Urological Association (KANEHARA & Co., LTD., Tokyo, 2003) or the WHO laboratory manual for the examination and processing of semen, 5th ed. (published by the World Health Organization, translated by the Institute for Advanced Reproductive Medical Technology, 2010). In a semen examination-a method of measuring the percentage of sperm with motility according to the above literatures, about 100 individuals of sperm are classified into 4 categories including: (A) sperm which move rapidly and linearly; (B) sperm which move slowly or poorly move linearly; (C) non-progressive sperm whose head or tail motility is found; and (D) immotile sperm which do not move. In principle, the percentage (%) of sperm with motility (A+B+C)/(A+B+C+D) was calculated as an average as obtained by repeating the above examination two or three times. Then, the improvement in the motility of sperm means that the percentage is significantly increased. Here, as used herein, the percentage of sperm with forward motility is represented by the formula: (A+B)/(A+B+C+D).

Preferable examples of the above method of measuring the percentage of sperm with motility can include a method comprising: placing 10 µl of liquid semen onto a counting broad while the temperature is desirably kept at 37° C.; covering with a cover glass; classifying about 100 individuals of sperm that reside in 5 or more sites in the visual field into the above 4 categories under microscopic examination with magnification of 200× or 400×; and repeating the examination, in principle, 2 to 3 times to calculate an average. In addition, a sperm solution as prepared by diluting semen to an appropriate concentration with physiological saline, a culture solution, or a buffer solution, etc., can be used as an alternative for the above semen.

Preferably, the above sperm is collected by a method according to the sample collection protocol described in the above Semen Examination Standardization Guideline or WHO laboratory manual for the examination of semen. Specifically, sperm can be collected into a clean glass or plastic wide mouth container by masturbation at a specialized semen collection site from a male patient after an abstemious period of at least 2 days and at most 7 days. This consists of one preparation step to prepare sperm (ejaculated sperm) in a semen sample taken within 4 hours after ejaculation, preferably within 3 hours, more preferably within 2 hours, and most preferably within 1 hour. Also, sperm (testicular sperm) can be collected by a testicular sperm extraction or a microdissection testicular sperm extraction. These sperm can be a preferable example.

In addition, the sperm that is subjected to freezing treatment and stored after the collection using these procedures are particularly preferable from the viewpoint of reducing the burden caused by sperm collection from a male patient. Accordingly, the effects of the present invention can be exerted. The conditions of the freezing treatment are not particularly limited, but examples can include a method comprising: suspending retrieved sperm in a cryopreservation buffer such as a TEST Yolk Buffer (Refrigeratin Medium, Irvine Scientific, CA, USA); then dispensing the suspension into cryotubes; and freezing them in liquid nitrogen. Examples of a sperm thawing protocol can include a method of heating and thawing sperm by placing a sperm-containing cryotube in warm water at 37° C. The freeze-thawed sperm, like sperm subjected to no freezing treatment, can be used in the method of enhancing the motility of sperm according to the present invention.

The most preferable example of the origin of the above sperm can be a human. However, the other examples can include common mammals, which are usually used as experimental animals, livestock, and pets, such as a rat, a mouse, a rabbit, a sheep, a pig, a cow, a horse, a goat, a cat, a dog, and a monkey. In the case of a large animal such as a cow, a horse, and a pig, preferable sperm can be retrieved by methods including an artificial vagina method, electric stimulation, massage of the ampulla of ductus deferens, and palm pressing.

Examples of the agent for improving sperm-motility consisting of a gas containing hydrogen molecules in an amount of 1% (v/v) or higher according to the present invention can include a mixed gas in which the lower limit of the concentration of the hydrogen gas is preferably 10% (v/v) or higher, more preferably 20% (v/v) or higher, still more preferably 30% (v/v) or higher, and still more preferably 40% (v/v) or higher. Meanwhile, the upper limit of the concentration of the hydrogen gas should be determined in light of safety considerations. Under safe conditions in which care is taken such that no static electricity occurs under a tightly sealed condition, 100% (v/v) does not give any trouble. In view of practical aspects, however, the concentration of the hydrogen gas is 80% (v/v) or lower and preferably 60% (v/v) or lower. Particularly preferable examples can include a mixed gas containing a hydrogen gas in an amount of between 45 and 55% (v/v). Examples of a gas component other than the hydrogen gas in such a mixed gas can include an oxygen gas, a carbon dioxide gas, and an inert gas. Examples of the inert gas can include a nitrogen gas, a helium gas, and an argon gas. However, preferred is a nitrogen gas, which is inexpensive and a component of the air. The content of the gas component other than the hydrogen gas can be optionally determined by those skilled in the art. However, preferred is a mixed gas containing 50% of hydrogen gas, 25% of nitrogen gas, 20% of oxygen gas, and 5% of carbon dioxide gas.

Examples of the agent for improving sperm-motility consisting of a liquid containing hydrogen molecules in an amount of 1% or higher of the saturation solubility thereof can include a liquid in which a hydrogen gas or a hydrogen-containing mixed gas is dissolved by bubbling, etc., into physiological saline, a culture solution, a buffer solution, etc. When the partial pressure of hydrogen is 0.101 MPa (1 atm) at 20° C., the solubility of the hydrogen molecules is 0.00162 g per 1000 g of water (about 1.6 ppm, 0.8 mM). However, preferred is large hydrogen solubility, that is, the case where the hydrogen gas is dissolved until a supersaturation state is generated. When a hydrogen-containing mixed gas containing hydrogen molecules in an amount of 50% is used for bubbling of a liquid, the hydrogen solubility is about 0.4 mM. The above physiological saline is not particularly limited as long as saline containing 0.9% (w/v) of sodium chloride is used. A culture solution prepared for in vitro fertilization is desirable as the above culture solution. Examples can include those developed as a human embryo-specific culture solution such as Cleavage Medium (SAGE (registered trademark) Cleavage Medium, CooperSurgical, Inc., CT, USA) supplemented with 10% plasma protein fraction (PPF), sperm washing medium (Irvine Scientific, CA, USA), fertilization (HTF) medium (SAGE In-Vitro Fertilization, CT, USA), and Ferticult (registered trademark) Sperm Washing Flushing Medium (FertiPro N. V., Beernem, Belgium). In addition, examples of the above buffer solution can include: a modified human tubal fluid culture medium (HTF) solution in which 20 mM HEPES (4-(2-hydroxyethyl)-1-piperazineethanesulfonic acid) is added to the HTF to have a buffer action; and phosphate buffered saline (PBS). Also, the most preferable examples can include the above culture solution and buffer solution supplemented with 10% heated human plasma protein (plasma protein fraction (PPF), Baxter, Inc., CA, USA). The above PPF is desirably inactivated by ethanol fractionation, heat treatment, S/D treatment, etc.

The liquid agent for improving sperm-motility according to the present invention can be provided as a container (bottle) containing a liquid into which hydrogen molecules are dissolved, preferably a sterile liquid. Examples of a method of manufacturing such an in-container liquid agent for improving sperm-motility can include: a method of filling a hydrogen impermeable material-made container with a hydrogen gas-containing liquid; and a method of keeping a liquid-containing, hydrogen permeable material-made container under a hydrogen gas atmosphere. Examples of the method of keeping it under a hydrogen gas atmosphere can include a method of putting a liquid-containing, hydrogen permeable material-made bottle in a hydrogen impermeable material-made package.

Examples of the above hydrogen impermeable material can include aluminum (can, foil), aluminum alloy (can, foil), carbon FRP in which high-strength carbon fiber impregnated with an epoxy resin is wound all around an aluminum liner, an aluminum pouch in which a synthetic resin film is laminated with (press-fitted to) aluminum foil, and a laminate in which aluminum foil is sandwiched between a paper and a polyethylene member. In addition, examples of the hydrogen permeable material can include PET (polyethylene terephthalate polyester), polyethylene, polypropylene, an ethylene-vinyl acetate copolymer, and a cyclic olefin copolymer.

The method of enhancing the motility of sperm according to the present invention is not particularly limited as long as the method comprises contacting the gaseous or liquid agent for improving sperm-motility according to the present invention with sperm in vitro. In order to contact the gaseous agent for improving sperm-motility with sperm, a sperm suspension in a thin film state is placed in a treatment container (for enhancing the motility of sperm) equipped with a port for introducing a hydrogen molecule-containing gas and a port for discharging the introduced gas. Then, the introduction of the gaseous agent for improving sperm-motility is made to continue for a prescribed duration, for example, 1 to 60 minutes. By doing so, the air inside the container is replaced by the gaseous agent for improving sperm-motility. After that, the sperm suspension is left to stand in the container for a prescribed duration, for example, 10 to 120 minutes, so that the gas can be equilibrated. Alternatively, in order to contact the liquid agent for improving sperm-motility with sperm, the liquid agent for improving sperm-motility can be used as a washing solution or diluent for semen. The contact between the agent for improving sperm-motility and the sperm can be carried out a plurality of times with a given interval such as from 12 to 48 hours. When the treatment using the agent for improving sperm-motility is repeated, the sperm can regain their motility.

Hereinafter, the present invention will be more specifically described with reference to Examples. The technical scope of the present invention, however, is not limited to these Examples. The sperm used in the following Examples were used for the purpose of research approved in the institutional review board (IRB) under the consent of patients undergoing infertility treatment at the "Yamashita Shonan Yume Clinic".

EXAMPLES

Example 1

1. Sperm Collection and Adjustment

Ejaculated sperm were collected by masturbation from male patients after an abstemious period of 3 days or more and 7 days or less. The semen transferred to the clinic within 4 hours after the ejaculation was diluted with SAGE (registered trademark) Cleavage Medium (CooperSurgical, Inc., CT, USA) supplemented with 1.5 ml of 10% PPF, which medium is gas-equilibrated at 37.5° C. with 5% carbon dioxide ($CO_2$), 5% oxygen ($O_2$), and 90% nitrogen ($N_2$) for 24 hours. The diluted semen was layered on an 80% Sperm Filter and then on 60% Sperm Filter in a 15-ml centrifuge tube and was subjected to centrifugation under conditions at 600 g×15 min. After the centrifugation, the supernatant was discarded, and the resulting precipitated pellet was diluted with 6 ml of the Cleavage Medium supplemented with 10% PPF. Then, centrifugation was performed under conditions at 400 g for 5 min. Subsequently, the supernatant was discarded, and the Cleavage Medium supplemented with 10% PPF was added to the resulting precipitated pellet. When used for in vitro fertilization, the mixture was diluted to the concentration of $1\times10^6$ sperm/ml. When used for micro-insemination, the mixture was adjusted such that the final volume was 0.05 ml.

When the following Examples 2 to 8 were examined, used was a sperm suspension obtained by storing, at room temperature for 5 days or more, the sperm suspension that was the rest after use in in vitro fertilization or micro-insemination.

Example 2

2. Treatment Using Gaseous Agent for Improving Sperm-Motility

The sperm suspension was grouped into 3 groups: an untreated group, a group of treatment with a mixed gas consisting of 5% $CO_2$, 20% $O_2$, 50% hydrogen ($H_2$), and 25% $N_2$ (hereinafter, referred to as an $H_2$ treatment group), and a group of treatment with a mixed gas consisting of 5% $CO_2$, 20% $O_2$, and 75% $N_2$ (hereinafter, referred to as an $N_2$ treatment group). The percentage of sperm with motility (the percentage of sperm with forward motility and the percentage of sperm with non-forward motility) and the percentage of immotile sperm were compared between the groups. The $H_2$ gas-containing mixed gas was prepared as follows: an MIGM incubation gas mixer (Tokken Inc., Chiba, Japan) and a flowmeter were used to adjust a 5% $CO_2$ gas and a 20% $O_2$ gas. After the flow rates of 5% $CO_2$ and 20% $O_2$ gases were found to be stable, a port of an $H_2$ gas cylinder was opened. Then, the $H_2$ gas was made to pass through water in a hermetically sealed flask to prepare an $H_2$ gas-containing mixed gas in the flask. After that, a passage connected to the flask was attached to an acryl box and the $H_2$ gas-containing mixed gas was made to enter the hermetically sealed acryl box. To check whether or not the gas passed through the acryl box, another passage was inserted into a water-containing beaker. Whether the gas passed therethrough was confirmed by observing the occurrence of bubbling via the passage in the beaker. With regard to the $N_2$ gas, the procedure was likewise performed and all were carried out at room temperature. A hundred μl of the sperm suspension was added dropwise to a 1008 dish. Before the mixed gas was made to pass therethrough, the dish was placed in the acryl box. The $H_2$ treatment group and the $N_2$ treatment group were each treated for 40 min. After 40 min had passed, each sperm suspension was well mixed by pipetting. Next, several μl of the sperm suspension was added dropwise to a Makler container. Then, the sperm concentration, the number of sperm with forward motility, the number of sperm with non-forward motility, and the number of immotile sperm were determined visually. Also, with respect to the untreated group in which the sperm suspension was used as it was, the sperm concentration, the number of sperm with forward motility, the number of sperm with non-forward motility, and the number of immotile sperm were likewise determined visually. In the above examination, the sperm that had a passage of five days or more after collection and lost almost all the motility were used as a test sample. Samples of the untreated group in which the percentage of sperm with forward motility exceeded 15% were excluded. Regarding the rest samples, one sample was grouped into three treatment groups and each treatment group was measured twice. Specifically, with respect to each sample, the ratio of the number of sperm with forward motility to the total number of sperm in the visual field was defined as the percentage of sperm with forward motility. The ratio of the number of sperm with some motility (a moving flagellum), but without forward motility to the total number of sperm was defined as the percentage of sperm with non-forward motility. The ratio of the number of sperm without motility to the total number of sperm was defined as the percentage of immotile sperm.

Example 3

3. Results of Measuring Percentage of Sperm with Forward Motility

FIG. 3(a) shows the percentage of sperm with forward motility with respect to each treatment group. In FIG. 3(a), the percentage of sperm with forward motility for the untreated group was an average of 3.6%. Also, the percentage of sperm with forward motility for the $N_2$ treatment group was an average of 7.7%. By contrast, the percentage of sperm with forward motility for the $H_2$ treatment group was increased to 16.8%. Next, when the recovery of the motility of each sample was examined, 12 samples (40%) of 30 samples with respect to each of the $H_2$ and $N_2$ treatment groups did not exhibit the recovery of forward motility. Of the 12 samples with respect to the $H_2$ treatment group in which the forward motility was not recovered, there were 3 samples (25%) of sperm with non-forward motility (without forward motility, but with a moving flagellum) while subjected to the $H_2$ treatment. Regarding the sperm in which the $H_2$ treatment did not result in the recovery of the motility of the sperm, their flagella were not straight and most of them had a spiral shape before the treatment. By contrast, the flagella of the sperm with forward motility and the sperm with non-forward motility, the motility of which was recovered after the $H_2$ treatment, were straight. The spiral-shaped sperm were determined to be dead sperm by PI (propidium iodide) fluorescence staining.

In 17 samples (94%) of 18 samples in which the forward motility was recovered, the $H_2$ treatment group exhibited a longer migration distance (i.e., increased forward motility) (P<0.01) than the $N_2$ treatment group. Six samples (35%) of the 17 samples in which the $H_2$ treatment group exhibited higher forward motility than the $N_2$ treatment group did not show the recovery of the forward movement in the untreated group and the $N_2$ treatment group. The forward movement was recovered only in the $H_2$ treatment group.

FIG. 4 shows the percentage of sperm with forward motility with respect to the individual samples. In 16 samples of the 17 samples obtained from patients in which the percentage of sperm with forward motility was less than 15%, the $H_2$ treatment was found to increase the percentage of sperm with forward motility. By contrast, in the $N_2$ treatment group, the percentage of sperm with forward motility was increased in four samples. Any of these four samples was a sample in which the $H_2$ treatment also caused the percentage of sperm with forward motility to increase. In addition, the percentage of sperm with forward motility for the $H_2$ treatment group was an average of 11%. By contrast, in the $N_2$ treatment group, the percentage was an average of 3.6%. Collectively, the $H_2$ treatment was demonstrated to effectively improve the motility of sperm.

Example 4

4. Results of Measuring Percentage of Sperm with Forward Motility

With regard to the sperm that were on day 5 after collection from 10 patients and were treated in each condition, the migration distance during 10 s of their forward movement was measured by video recording. Then, the recorded video was analyzed by the CASA system (NIH) (computer assisted sperm analysis using ImageJ, description of necessary components and use of free software) to determine the migration distance of forwardly moving sperm. The results are shown in FIG. 5. In the patients, there was no significant difference (P=0.2193) when the average migration distance was compared among the untreated (control) group, the $H_2$ treatment group, and the $N_2$ treatment group. This indicates that the $H_2$ treatment does not affect the velocity of the forwardly moving sperm. In addition, this demonstrated that the migration distance per second of the sperm in the $H_2$ treatment group was the longest one.

Example 5

5. Results of Measuring Percentage of Sperm with Forward Motility with Respect to Each Duration of $H_2$ Treatment The relationship between the duration of $H_2$ treatment and the percentage of sperm with forward motility was compared among individual patients. FIG. 3(b) shows the results of comparing the percentage of sperm with forward motility in the individual patients when the duration of $H_2$ treatment was 5, 30, or 60 min. When the duration of $H_2$ treatment was 5 min, it was demonstrated that the percentage of sperm with forward motility rather tended to decrease when compared with that of the control (untreated) group. When the duration of $H_2$ treatment was 30 or 60 min, the percentage of sperm with forward motility was higher in about 70% of the samples than in the control. This demonstrated that 30 min of the $H_2$ treatment sufficiently improved the motility of sperm.

Example 6

6. Time Course of Number of Sperm with Motility by $H_2$ Treatment and $H_2$ Retreatment FIG. 6 shows the time course (after 30, 60 min) of the percentage of sperm with forward motility after the sperm on day 5 after collection from 10 patients were treated with $H_2$ (30 min). When 10 min passed after 30 min of the $H_2$ treatment, the hydrogen in 10 µl of the suspension was eliminated. However, even after 30 to 150 min, a big change in the forward motility of sperm was not observed. This indicates that the sperm that regain the motor function after the $H_2$ treatment can be used for micro-insemination as they are. When the $H_2$ retreatment (30 min) was carried out at 24 hours after the $H_2$ treatment (30 min), the $H_2$-treated sperm had motility even after 24 hours.

Example 7

7. Treatment Using Liquid Agent for Improving Sperm-Motility

A liquid agent for improving sperm-motility was prepared by subjecting 6 ml of a culture solution for washing sperm to 10-min bubbling with a hydrogen-containing mixed gas (5% $O_2$, 5% $CO_2$, 40% $N_2$, and 50% $H_2$). Hydrogen was dissolved in the culture solution by bubbling. In this case, measurements were performed using a hydrogen electrode manufactured by UNISENSE Co., Ltd. The results showed that the concentration of hydrogen was 300 µM at 10 min after the bubbling and the equilibrium was achieved. Next, the culture solution was left to stand. When measured, the concentration of hydrogen showed a gradual decrease and was 50 µM after 3 hours. The culture solution as so prepared was used to wash sperm, and a change in their motility was examined. Here, the percentage of sperm with forward motility before washing was 0%. By contrast, when the culture solution that was subjected to bubbling with a hydrogen-containing mixed gas was used for the washing for 5 min, the percentage of sperm with forward motility was increased to 47%. In addition, after centrifugation at 400 g×5 min during the washing step, the concentration of hydrogen after 5 min was 150 µM. After re-centrifugation, the concentration was decreased to 100 µM. This demonstrated that the centrifugation was a factor that caused hydrogen to be purged out from the culture solution. FIG. 3(b) showed that the 5-min treatment using the gaseous agent for improving sperm-motility did not result in the recovery of the motility of sperm. By contrast, it was demonstrated that the 5-min washing treatment using the liquid agent for improving sperm-motility augmented the motility of sperm.

Example 8

8. $H_2$ Treatment Increases Mitochondrial Membrane Potential

By using the sperm suspensions of the untreated group, the $H_2$ treatment group, and the $N_2$ treatment group, mitochondria of sperm were co-stained for 30 min with 2 µM of tetramethyl rhodamine methyl ester (TMRM; Life Technologies, CA, USA) and 2 µM of MitoTracker Green (MTG; Life Technologies, CA, USA). While the MTG fluorescence has nothing to do with the membrane potential, the TMRM fluorescence is known to depend on the mitochondrial membrane potential. The stained sperm were visualized using a laser scanning confocal microscope (Leica, Wetzlar, Germany). In addition, the viability of sperm was checked by PI fluorescence staining.

The results of co-staining are shown in FIGS. 7(a) to (c). FIGS. 7(a), (b), and (c) show the untreated group, the $H_2$ treatment group, and $N_2$ treatment group, respectively. Meanwhile, the differential interference images were designated as DIC (Differential interference contrast). The bars indicate 10 µm. FIG. 7(d) is a graph showing the results of semi-quantifying, using the ImageJ, the fluorescent intensity of the sperm stained with TMRM. When compared with the untreated group and the $N_2$ treatment group, the $H_2$ treatment group showed a strong intensity of TMRM fluorescence (P<0.001). The motility of sperm depends on the ATP content. It was demonstrated that the intensity of TMRM fluorescence depending on the mitochondrial membrane potential was higher in the sperm of the $H_2$ treatment group than in those of the other groups. This suggests that the $H_2$ treatment should increase the function of sperm mitochondria, thereby enhancing the motility.

Example 9

9. $H_2$ Treatment of Freeze-thawed Sperm Increases Motility

Ejaculated sperm were collected by masturbation from male patients after an abstemious period of 3 days or more and 7 days or less. Semen that was transferred to the clinic within four hours after ejaculation was suspended in a solution in which equal amounts of the Cleavage Medium and TEST-yolk buffer (TYB; Irvine Scientific, CA, USA) had been mixed. Then, the mixture was dispensed into cryotubes. The resulting cryotubes were once exposed to nitrogen vapor for 5 min, and were then cryopreserved in liquid nitrogen. At the time of thawing, each cryotube was heated in warm water at 37° C. After that, the sperm suspension in the cryotube was dispensed into four vials.

The Cleavage Medium saturated with $H_2$ and the Cleavage Medium equilibrated with 5% $CO_2$ were mixed to prepare a sperm washing medium. The sperm washing medium in which the mixing ratio of $H_2$-saturated Cleavage Medium was 50%, 75%, or 100% was prepared. After the dispensed sperm suspension was washed for 5 min with each sperm washing medium, the motility of sperm was measured.

FIG. 8 shows the results of measuring the motility of freeze-thawed sperm. In FIG. 8(a), the subjects are 6 samples obtained from patients in which the percentage of sperm with forward motility was 50% or higher. In FIG. 8(b), the subjects are 15 samples obtained from patients in which the percentage of sperm with forward motility was less than 50%. In FIG. 8(a), without the $H_2$ treatment, the percentage of sperm with forward motility was an average of 27.5%. However, after the treatment with the washing medium containing 50% of $H_2$, the percentage was increased to 61.3%. After the treatment with the washing medium containing 75% of $H_2$, the percentage was increased to 71.0%. Also, after the treatment with the washing medium containing 100% of $H_2$, the percentage was increased to 70.0%. In FIG. 8(b), without the $H_2$ treatment, the percentage of sperm with forward motility was an average of 61.3%. However, after the treatment with the washing medium containing 50% of $H_2$, the percentage was increased to 41.2%. After the treatment with the washing medium containing 75% of $H_2$, the percentage was increased to 40.8%. Also, after the treatment with the washing medium containing 100% of $H_2$, the percentage was increased to 31.4%.

This has demonstrated that the $H_2$ treatment effectively and markedly improves the motility, which has been low, of freeze-thawed sperm.

INDUSTRIAL APPLICABILITY

The present invention provides an agent for improving sperm-motility for immotile sperm which are considered to be dead sperm in male infertility treatment. In cases represented by asthenospermia, the present invention causes the motor function of immotile sperm to be recovered and should therefore increase the conception rate during micro-insemination-embryo transfer therapy.

EXPLANATION OF LETTERS OR NUMERALS

1 Sperm-motility improving treatment container
2 Gas mixer
3 Hydrogen gas cylinder
4 Cylinder containing gas other than hydrogen gas
5 Piping

The invention claimed is:

1. A method for improving sperm forward motility, comprising contacting in vitro a liquid comprising a hydrogen molecule in an amount of 1% (v/v) or higher of a saturation solubility thereof, with a sperm having a reduced percentage of sperm with forward motility, derived from male infertility patients, wherein the liquid is suitable for in vitro fertilization or micro-insemination.

2. The method according to claim 1, wherein the liquid is a liquid in which the hydrogen molecule is dissolved by bubbling.

3. The method according to claim 1, wherein the liquid is physiological saline, a culture solution, or a buffer solution, comprising a hydrogen molecule.

4. The method according to claim 1, wherein the liquid is stored in a container.

5. The method according to claim 1, wherein the sperm is a cryopreserved sperm.

6. The method according to claim 1, comprising contacting the liquid with the sperm a plurality of times.

7. The method according to claim 2, wherein the liquid is physiological saline, a culture solution, or a buffer solution, comprising a hydrogen molecule.

8. The method according to claim 2, wherein the liquid is stored in a container.

9. The method according to claim 1, wherein the sperm is a sperm in which the percentage of sperm with forward motility is less than 15%.

* * * * *